United States Patent [19]

Blancou et al.

[11] Patent Number: 4,906,416
[45] Date of Patent: Mar. 6, 1990

[54] PREPARATION OF PERFLUOROALKANECARBOXYLIC ACIDS AND NOVEL PERFLUOROALKANEDICHLOROETHYLENES OBTAINED

[75] Inventors: Hubert Blancou, Montpellier; Auguste Commeyras, Clapiers; Robert Teissèdre, Montpellier, all of France

[73] Assignee: Atochem, Courbevoie, France

[21] Appl. No.: 699,827

[22] Filed: Feb. 8, 1985

[30] Foreign Application Priority Data

Feb. 14, 1984 [FR] France .................................. 84 02195

[51] Int. Cl.$^4$ .............................. C09F 7/02; C11C 1/00
[52] U.S. Cl. .................................. 260/408; 562/541; 570/135; 570/153
[58] Field of Search ................... 562/541; 260/408; 570/135, 153

[56] References Cited

U.S. PATENT DOCUMENTS

| | | | |
|---|---|---|---|
| 2,371,757 | 3/1945 | Henne | 562/541 |
| 2,628,988 | 2/1953 | Ruh | 570/135 |
| 2,634,301 | 4/1953 | Ruh | 570/135 |
| 3,046,304 | 7/1962 | Neville | 570/135 |
| 3,525,758 | 8/1970 | Katsushima et al. | 260/408 |
| 4,478,760 | 10/1984 | Blancou et al. | 260/408 |

Primary Examiner—Werren B. Lone
Attorney, Agent, or Firm—Brooks Haidt Haffner & Delahunty

[57] ABSTRACT

A process for preparing perfluoroalkanecarboxylic acids, wherein a perfluoroiodoalkane, $R_FI$, is reacted with trichloroethylene in an acidic solvent in the presence of zinc, and the 2-perfluoroalkyl-1,1-dichloroethylene thus obtained is oxidized with the aid of permanganate, $R_F$ representing a straight chain or branched perfluoro radical containing one to 20 carbon atoms, together with certain novel perfluoroalkyldichloroethylenes having four or more carbon atoms so obtained.

8 Claims, No Drawings

PREPARATION OF PERFLUOROALKANECARBOXYLIC ACIDS AND NOVEL PERFLUOROALKANEDICHLOROETHYLENES OBTAINED

BACKGROUND OF THE INVENTION

The present invention relates to the preparation of perfluoroalkanecarboxylic acids, and more particularly, it relates to the preparation of such acids with the formula $R_FCOOH$, wherein $R_F$ is a straight-chain or branched perfluoroalkyl radical containing from one to 20 carbon atoms, through intermediate perfluoroalkanedichloroethylenes, some of which are novel.

These acids, the salts of which are employed as surface-active agents in tetrafluoroethylene polymerization or as emulsifiers in foams for firefighting, are prepared commercially by electrofluorination of alkanesulfonic acid chlorides or by hydrolysis of perfluoroiodoalkanes, $R_FI$, with oleum. However, this latter method results in the loss of two fluorine atoms per molecule of the perfluoro-iodo derivative.

THE INVENTION

An advantageous process for the manufacture of such perfluoroalkanecarboxylic acids has now been discovered. The process according to the invention comprises reacting a perfluoroiodoalkane, $R_FI$, with trichloroethylene in an acidic solvent in the presence of zinc, and then oxidizing the 2-perfluoroalkyl-1-dichloroethylene, $R_FCH=CCl_2$, thus obtained with a permanganate, desirably sodium or potassium permanganate. The process of this invention also provides novel perfluoroalkanedichloroethylene intermediates having four or more carbon atoms.

In this process, which can be represented schematically as follows:

$$R_FI + ClHC=CCl_2 \xrightarrow{Zn}_{Acid}$$

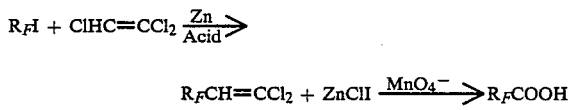

$$R_FCH=CCl_2 + ZnClI \xrightarrow{MnO_4^-} R_FCOOH$$

the perfluoroiodoalkane and trichloroethylene can be employed in stoichiometric amounts. However, to limit the formation of by-products (essentially the perfluorohydroalkane, $R_FH$, and the perfluoroalkane, $R_F—R_F$), it has been found advantageous to use trichloroethylene in amounts of about two moles with respect to the amount of perfluoroiodoalkane.

The reaction of the perfluoroiodoalkane with trichloroethylene is carried out in an acidic solvent which can be an organic acid, a dilute mineral acid, or a mixture of an organic or inorganic acid and an organic solvent. The organic acids can be aliphatic acids such as formic, acetic, and the like. The dilute mineral acid can be, for example, ten percent hydrochloric acid. The organic solvents can be aromatic or oxygenated solvents such as benzene, toluene, dioxane, and the like. In certain embodiments, propionic acid is a preferred acidic solvent. The quantity of acidic solvent to be used can be varied within wide limits, depending on the nature of the perfluoroiodoalkane employed and on the activation of the zinc. The quantity of acidic solvent is desirably from about 100 to 1000 ml per mole of perfluoroiodoalkane.

The zinc employed in this process is commercial zinc powder. It can be desirable in some embodiments to activate this powder using methods which are well known in the art, e.g., see Houben-Weyl, 1973, XIII 2a, pages 570 to 574 and 815. Thus, for instance, the zinc can be activated by attack with a strong inorganic acid such as hydrochloric acid or sulfuric acid or by the formation of alloys with other metals such as lead, mercury or copper. The process of the present invention utilizes a stoichiometric quantity of zinc, but it is advantageous in certain embodiments of the invention to employ an excess of zinc (5 to 50 percent, and in certain preferred embodiments about 10 percent) relative to the perfluoroiodoalkane.

The reaction of the perfluoroiodoalkane with trichloroethylene is advantageously carried out at ambient pressure and temperature. However, if desired, it is possible to operate at a higher temperature which can range up to the boiling point of the reaction mixture.

This reaction may be carried out with agitation. However, it has been found that the proportion of by-products formed is lower when the mixture is not subjected to stirring and when the reaction is carried out in propionic acid with the molar ratio of trichloroethylene/$R_FI$ equal to two. The reaction then proceeds by slow diffusion of propionic acid into the $R_FI/CHCl=CCl_2$ mixture.

The products obtained can be isolated from the reaction mixture by suitable conventional means such as washing with water, decantation, extraction, distillation, filtration, and the like.

2-Trifluoromethyl-1,1-dichloroethylene and its use as an anesthetic are already known. See, for example, J. Am. Chem. Soc. 64, 1157–9; J. Mol. Spectroscopy 7, 385; and Anesthesiology 14, 466. A compound of empirical formula $C_4HCl_2F_5$, obtained by distillation of the crude product of fluorination of polychlorobutanes, is described in the work "Preparation, Properties and Technology of Fluorine and Organic Fluoro Compounds", McGraw-Hill 1951, at pages 770–5. The 2-perfluoroalkyl-1,1-dichloroethylenes in which the perfluoroalkyl radical contains from four to 12 carbon atoms are new and, as such, form part of the present invention.

Oxidation of 2-perfluoroalkyl-1,1-dichloroethylenes to perfluoroalkanecarboxylic acids is carried out in a basic aqueous medium. The most convenient alkaline agent used is sodium carbonate. The oxidation is carried out at a temperature which is at least 80° C. and can range up to the boiling point of the reaction mixture (approximately 100° C.).

All parts, percentages, proportions and ratios herein are by weight unless otherwise stated.

The following Examples are given to illustrate embodiments of the invention as it is presently preferred to practice it. It will be understood that these Examples are illustrative, and the invention is not to be considered as restricted thereto except as indicated in the appended claims.

EXAMPLE I

Zinc powder in the amount of 6.4 g (0.11 mole) is suspended with stirring in a mixture of 26 g (0.2 mole) of trichloroethylene and 30 ml of propionic acid. Then, 44.6 g (0.1 mole) of $C_6F_{13}I$ is added to this dispersion over two hours. The reaction is exothermic.

At the end of the reaction, the mixture is treated with water and, after the phases have separated, the organic phase is washed serially with a 20% strength solution of hydrochloric acid, then with a 20% strength solution of sodium carbonate, and finally with water. After vacuum distillation, 29 g of 2-perfluorohexyl-1,1-dichloroethylene, b.p.: 105° C. at 20 mm Hg, is obtained, for a yield of 69%.

Analysis of the reaction mixture by $^{19}$F-NMR (nuclear magnetic resonance) shows the presence, respectively, of 80 mole percent of 2-perfluorohexyl-1,1-dichloroethylene, 15 mole percent of perfluorohydrohexane ($C_6F_{13}H$), and 5 mole percent of perfluorododecane ($C_{12}F_{26}$).

The 2-perfluorohexyl-1,1-dichloroethylene is identified by $^{19}$F-NMR, $^1$H-NMR, IR (infrared), and mass spectrometry.

EXAMPLE II

The procedure of Example I is repeated but with only 13.2 g (0.1 mole) of trichloroethylene. Analysis of the reaction mixture by $^{19}$F-NMR shows the presence of 35 mole percent of $C_6F_{13}CH=CCl_2$, 42 mole percent of $C_6F_{13}H$, and 23 mole percent of $C_{12}F_{26}$.

EXAMPLE III

The procedure of Example I is repeated but with 39.6 g (0.3 mole) of trichloroethylene. Analysis of the reaction mixture by $^{19}$F-NMR shows the presence of 65 mole percent of $C_6F_{13}CH=CCl_2$, 15 mole percent of $C_6F_{13}H$, and 20 mole percent of $C_{12}F_{26}$.

EXAMPLE IV

Zinc, trichloroethylene and perfluoroiodohexane are successively introduced, followed by propionic acid, in the same proportions as in Example I into a small cross-section (40 mm diameter) cylindrical vessel. The mixture is left without stirring for 24 hours. It is then treated, as in Example I, successively with $H_2O$, HCl, $Na_2CO_3$ and water. The organic phase is then distilled, and 37 g of 2-perfluorohexyl-1,1-dichloroethylene are collected. The yield is 89%.

Analysis of the reaction mixture by $^{19}$F-NMR shows the presence of 90 mole percent 2-perfluorohexyl-1,1-dichloroethylene and 10 mole percent perfluorohydrohexane.

EXAMPLES V to VII

The following Table I summarizes the results of products obtained by operating as in Example I, but with the propionic acid respectively replaced by a 10% aqueous solution of hydrochloric acid (Example V), by pure acetic acid (Example VI), and by formic acid (Example VII). The precentages are on a molar basis:

|  | EXAMPLE | | |
| --- | --- | --- | --- |
|  | V | VI | VII |
| $C_6F_{13}CH=CCl_2$ | 30% | 77% | 59% |
| $C_6F_{13}H$ | 35% | 23% | 5% |
| $C_{12}F_{26}$ | 33% | — | 21% |
| $C_6F_{13}I$ | 2% | — | 5% |
| Unidentified products | — | — | 10% |

EXAMPLE VIII

The procedure of Example I is repeated, but with $C_6F_{13}I$ replaced by 34.6 g (0.1 mole) of $C_4F_9I$. Eighty-five mole percent of $C_4F_9CH=CCl_2$, five mole percent of $C_4F_9H$, and ten mole percent of various unidentified products are thus obtained.

EXAMPLE IX

Five hundredths of a mole (20.8 g) of $C_6F_{13}CH=CCl_2$ is added to 15.8 g (0.1 mole) of $KMnO_4$ and 12 g of $Na_2CO_3.2H_2O$ in 30 ml of water. The reaction mixture is heated to 80° C. for three hours and then filtered, and the filtrate is treated with 5 ml of concentrated hydrochloric acid (400 g/L). The perfluorohexanecarboxylic acid separates out and is distilled. In this manner, 16 g of the acid $C_6F_{13}COOH$, identified by comparison with an authentic sample, is obtained. The yield is 88%.

EXAMPLE X

The procedure of Example IX is followed using the 2-perfluoro-butyl-1,1-dichloroethylene of Example VIII. The acid $C_4F_9COOH$ is obtained in the same manner.

It will be appreciated that among other uses, the novel 2-perfluoroalkyl-1,1-dichloroethylenes are useful as intermediates, particularly for the preparation of perfluorocarboxylic acid derivatives.

What is claimed is:

1. A process for the preparation of perfluoroalkanecarboxylic acids having the formula $R_FCOOH$, which process comprises reacting a perfluoroiodoalkane having the formula $R_FI$ with trichloroethylene in an acidic medium in the presence of zinc to form an intermediate 2-perfluoroalkyl-1,1-dichloroethylene having the formula $R_FCH=CCl_2$, and oxidizing the intermediate in a basic medium with an alkali metal permanganate at a temperature of at least 80° C., wherein $R_F$ represents a linear or branched chain perfluoroalkyl group having from one to 20 carbon atoms.

2. A process according to claim 1, wherein the molar ratio of trichloroethylene/perfluoroiodoalkane is about two.

3. A process according to claim 1, wherein the acidic medium is formic, acetic, or propionic acid or dilute hydrochloric acid.

4. A process according to claim 1, wherein the reaction of perfluoroiodoalkane with trichloroethylene is carried out without stirring.

5. A process according to claim 4, wherein the acidic medium is propionic acid.

6. A process according to claim 1, wherein the oxidation is carried out in the presence of sodium carbonate.

7. A process according to claim 1, wherein the perfluoroiodoalkane contains from four to 12 carbon atoms.

8. A process according to claim 1 wherein the alkali metal is sodium or potassium.

* * * * *